United States Patent [19]
Burlakov et al.

[11] Patent Number: 5,965,623
[45] Date of Patent: Oct. 12, 1999

[54] ANTI-GLUCOCORTICOID DRUG

[76] Inventors: Sergei Dmitrievich Burlakov, pr.Lunacharskogo, dom 58/2, kv.8, 194353, S-Petersburg, Russian Federation; Dmitry Dmitrievich Genkin, Kronversky pr., dom 73/79, kv.39, 197198, S-Petersburg, Russian Federation; Kirill Gennadievich Surkov, ul.Lermontova, dom 22, korp.2, kv.33, 198320, S-Petersburg, Russian Federation; Viktor Veniaminivich Tets, Nevsky pr., dom 114, kv.36, 191025 S-Petersburg, Russian Federation

[21] Appl. No.: 08/930,733

[22] PCT Filed: Feb. 1, 1996

[86] PCT No.: PCT/RU96/00028

§ 371 Date: Sep. 26, 1997

§ 102(e) Date: Sep. 26, 1997

[87] PCT Pub. No.: WO97/27845

PCT Pub. Date: Aug. 7, 1997

[30] Foreign Application Priority Data

Jan. 31, 1996 [RU] Russian Federation ............. 96101194

[51] Int. Cl.$^6$ ...................... A61K 31/045; A61K 31/685; A61K 31/11; A61K 31/08
[52] U.S. Cl. ............................ 514/739; 514/78; 514/724; 514/703; 514/722
[58] Field of Search .............................. 514/78, 724, 703, 514/722, 739

[56] References Cited

PUBLICATIONS

Bartelt et al.; J. Chem. Ecol., 9 (9), 1343–52 (Abstract), 1983.

Dunkelblum et al.; Insect Biochem., 19 (5), 523–6 (Abstract), 1989.

Sweeney et al. J. Chem. Ecol., 16(5), 1517–30 (Abstract), 1990.

*Primary Examiner*—Russell Travers
*Attorney, Agent, or Firm*—Ilya Zyborovsky

[57] ABSTRACT

Somatic mammary cells are defended from an action of glucocorticoid hormones by an insect pheromones of non-steroid nature, its derivative or a synthetic analog.

5 Claims, No Drawings

ANTI-GLUCOCORTICOID DRUG

BACKGROUND OF THE INVENTION

The invention relates to medicine, specifically to antiglucocorticoid preparations of a non-steroid nature, i.e. preparations whose chemical structure contains no steran nucleus. The purpose of the invention is to defend somatic mammary cells from the action of glucocorticoid hormones.

The following glucocorticoid-suppressive substances are known to be in use in medicine:

1. Substances which suppress the synthesis of steroid hormones at various stages (inhibitors of enzymes which catalyze various stages of the synthesis of steroid hormones [1]):
   a) derivatives of diphenylmethane, e.g. amphenon B (which suppresses the synthesis of steroid hormones at stages 11-β-, 17- and 21- of hydroxylase);
   b) derivatives of pyridine (SU-c series), e.g. metirapon (which suppresses synthesis at stage 11-β of hydroxylase);
   c) substituted α,α-glutaramides, e.g. aminoglutetimide (which impedes the synthesis of pregnenolon from cholesterine through suppression of 20-α-hydroxylase and C20, C-22-liase;
   d) steroid substances,
      e.g. trilostan (3β-substituted steroid-3β-hydroxy-5-androsten-17-one), which suppresses 3β-desoxysteroidhydrogenase-5.4-isomerase [4].
2. Substances which suppress the interaction of glucocorticoid hormones with hormone receptors:
   a) steroid substances,
      e.g. mifepriston (11β-substituted steroid derivative-11β-(4 dimethyl-aminophenyl)-17β-hydroxy-17α-(prop-1-inyll)-estra4.9dien-3-one), which acts on receptors of glucocorticoid hormones to form a complex incapable of initiating mechanisms of the glucocorticoid effect [3];
   b) non-steroid substances [2], e.g. drotaverina hydrochloride (a derivative of isoquinoline-1-(3.4-dietoxibenzilidene)-6.7-dietoxy-1,2,3,4-tetrahydrizoquinoline) or acetylsalicic acid [5].

The above-named preparations have a determinate antiglucocorticoid effect when taken as an ingredient in various medicines.

It is also known that the above-listed preparations have a number of significant drawbacks:

1. Preparations which inhibit the synthesis of glucocorticoids also inhibit, depending upon the target enzymes, the synthesis of other steroid hormones (i.e. sexual steroids and/or mineralocorticoids) and elicit an accumulation of the predecessor substrates of inhibited enzymes, which substrates also display hormonal activity.

2. The level of specificity of effect of preparations in the second group is very low, i.e. in addition to an antiglucocorticoid effect, they also have other steroidal antihormonal effects as well.

3. All steroid substances in one way or another upset the balance of steroids in the human organism. Such substances may form metabolites possessing active characteristics different to those of the substance initially administered to the patient.

Of the above-listed preparations Mifepriston (RU 486), a medicine containing a steran nucleus, is the most free of the above-named defects, is the most specific in its ability to block glucocorticoid receptors, and is closest in its pharmacological action to the group of medicines which are the subject of the present application. Mifepriston is described in greater detail in, for example, [3] and [6]. Hereafter in the present application Mifepriston will be used as the most frequent comparison for the effectiveness of the antiglucocorticoid medicine which is the subject of this application (hereinafter called 'the proposed drug'). Together with its great advantages, Mifepriston, like other analogues, possesses a number of weak points:

it is effective only in high doses (400 mg/day);
   its structure contains a steran nucleus;
   it affects receptors of sexual steroids, progestins and mineralocorticoids.

Also known are insect pheromones, i.e. substances produced and excreted into the environment by insects and having a specific smell that acts upon specific (pheromone) receptors in sensitive members of the same insect type, eliciting in the latter a typical behavioral reaction or process, e.g. attraction of insects of the opposite sex to a meeting site, preparations for fertilization etc. [8].

One group of pheromones comprises, specifically, long-chain aliphatic unsaturated alcohols, ethers and acetates containing in a linear hydrocarbon chain between 10 and 21 carbon atoms. Pheromones of this group are used as domestic and agricultural insecticides [7,8].

The specific physical and chemical characteristics of the above-named pheromones and their synthetic analogues and derivatives (specifically, the pronounced hydrophobic property of the long-chain hydrocarbon structure) give them the ability easily to dissolve in fats and to incorporate themselves into biological membranes, altering the physical and mechanical properties (liquidity, penetrability) of such membranes. The latter ability allows them to be used as an ingredient in preparations intended to enhance the transcutaneous penetrability of membranes [10].

The hydrophobic tendency of the given group of pheromones explains the use currently made in medicine and biology of the biological properties of such pheromones. Such properties are:

1) ANAESTHETIZING PROPERTIES, leading to the use of such pheromones as anaesthetics [11];
2) ABILITY TO SUPPRESS BACTERIA [12] AND VIRUSES [13,14], leading to their use for this purpose in medicine and biology;
3) ABILITY TO INDUCE LYSIS OF ERYTHROCYTES [15], leading to their use as inductors of lysis of erythrocytes [15].

Obviously, the above-described known properties of the given group of pheromones and of their synthetic analogues and derivatives, and the cosmetic, agricultural and biological uses of such pheromones, analogues and derivatives have no relation to glucocorticoid activity (detailed proof of this statement will be given below); this explains why none of the experts known to us has ever had an interest in the above-named substances from the point of view of using them to produce an antiglucocorticoid effect.

BRIEF DESCRIPTION OF THE INVENTION

The goals of the present invention are to: 1) eliminate the above-named drawbacks as typified in the antiglucocorticoid analogues named above; 2) create a new class of medicines such as: a) are capable of efficient and specific suppression of the effects of glucocorticoids; b) are suitable for the treatment of a broad range of pathological conditions; c) possess low toxicity and a high therapeutic index.

The above goals were met by using as an antiglucocorticoid medicine non-steroid insect pheromones (i.e. pheromones whose chemical structure contains no steran nucleus) or synthetic analogues of such pheromones comprising either an unsaturated long-chain aliphatic alcohol or an aldehyde or ether, which aliphatic alcohol or aldehyde or ether contains between 10 and 21 carbon atoms in a linear hydrocarbon chain.

The above selection was made on the basis of the results of investigations conducted by the authors of the invention, which investigations led to the discovery of new biological properties possessed by the given combinations; amongst such properties was the ability to suppress the receptor-mediated effect of glucocorticoids on somatic cells in the mammary glands.

It was these properties of the given combinations—properties of which the authors were unaware from the sources of information available to them—that permitted the realization of the goals in question.

Moreover, in order to enhance the therapeutic effect, use may be made of a mixture of several pheromones and/or their synthetic analogues. In this case the choice of substances for the mixture should be such as to give a large difference in the hydrophobic tendencies of the components (the hydrophobic tendency of a component is proportional to the length of that component's hydrocarbon chain): the difference in length between the hydrocarbon chains should be at least five.

In addition to the above, it should be said that the production of specific medicinal products may be simplified by using derivatives of pheromones and/or their synthetic analogues, selection of which should follow the same principles.

Medicines based on insect pheromones contain one, two or more medicinal substances mixed with apyretic water, a physiologically compatible buffer solution (or other pharmaceutically acceptable carrier) or enclosed in microcapsules (e.g. artificial lipid structures (liposomes) or other pharmaceutically acceptable carriers). Such medicines are manufactured in the form of tablets, capsules, indictable solutions, ointments et cetera.

The proposed medicinal structure makes it possible to produce medicines capable of effective and specific suppression of the functioning of glucocorticoid receptors, and suitable for treatment of a broad range of pathological conditions.

The feasibility of production of the proposed drug is demonstrated by the following practical examples.

EXAMPLE 1

Using 1 pheromone or its synthetic analogue. 500 mg. of lipids (dipalmitoylphosphatidylcholin, phosphatidylserin in a molar proportion of 10:0.1) and 100 mg. of Z-11-tetradecinol (unsaturated aliphatic spirit with hydrocarbon-chain length 14 and trans-double bond in position 11) are dissolved in 500 ml. of chloroform at 22° C. and placed in a thick-walled round-bottomed 4-liter flask. The flask is placed on a rotor vaporizer and the solvent is eliminated at 65° C. A thin semi-transparent film forms on the walls of the flask. The flask is put into a drying chamber equipped with a nitrogen trap, and is further dried in a vacuum for 1 hour. 10 ml. of twice-distilled deionized water are added to the flask. After the flask has been ventilated with helium, the film is rehydrated by vigorous shaking at 65° C. for 1 hour. As a result 10 ml. of thick gel with a greenish hue is formed. The gel is diluted using 90 ml. of phosphate buffer (pH=7.4, 22° C.) and shaken for 30 minutes at 22° C. As a result 100 ml. of suspension is formed. This suspension is subjected to ultrasound at 44 kHz 30 times for 30 seconds with intervals of 1 minute between shakes. The resulting suspension is compressed (twice, consecutively) under pressure of nitrogen through polycarbonate membranes the diameter of whose pores is first 500 and then 100 nanometers. An opalescent suspension is formed comprising an aqueous suspension of small monolayer liposomes of 80–130 nanometers in size, which liposomes contain 500 mg. of lipids and 100 mg. of Z-11-tetradecinol. 10 ml. of the suspension thus obtained is dispersed in 120 ml. of ointment base which has been heated to a temperature of 80° C. and which comprises vaseline, wax and sorbitol trioleat (in a proportion of 30:2:5). The cream thus obtained is packed into 2-gram tubes containing 1 mg. of Z-11-tetradecinol and 2 g. of liposomal cream.

EXAMPLE 2

Using 2 pheromones or their synthetic analogues. 100 mg. of Z-(9)-tetradecinol (unsaturated aliphatic ether with hydrocarbon-chain length 14 and trans-double bond in position 9) and 3 mg. of Z-11-heptadecinol (unsaturated aliphatic spirit with hydrocarbon-chain length 19 and trans-double bond in position 11) are dissolved in 500 ml. of sterile olive oil. The resulting solution is poured into bottles, which are then sterilized and hermetically sealed. This produces a medicine suitable for parenteral hypodermic) use.

EXAMPLE 3

Using 1 derivative of a pheromone (benzyl ether of aliphatic unsaturated spirit (Z-(14) heptadecinol). 500 mg. of lipids (phosphatidylcholin, phospatidylethanolamin, cholesterol in a molar proportion of 1:0.01:0.5) is dissolved in 400 ml. of diethyl ether at a temperature of 22° C. 50 mg. of Z-(14)-heptadecinilbenzoate is dissolved in 1 ml. of dimethylsulfoxide at 60° C. before being cooled to 22° C. and added in drops to 400 ml. of the solution of lipids in diethyl ether. The resulting solution is intensively mixed. 100 ml. of double-distilled water is added to the solution. The diphase system thus obtained is treated with ultrasound until the border dividing the two phases disappears and a disperse system (emulsion) forms. The organic phase is eliminated in a rotor vaporizer at a temperature exceeding the temperature of phase transition of the most refractory phospholipid (60° C.) among those present in the mixture; during the vaporizing process the vacuum is gradually increased to 0.1 tor. 100 ml. of thick gel is obtained. After freezing in liquid nitrogen, the gel is subjected to lyophilic drying, giving 550 mg. of powder. The powder is pressed into tablets, each of which contains 50 mg. of lipids and 5 mg. of Z-(14)-heptadecinilbenzoate. Alternatively, the powder may be packed into bottles, each of which contains 50 mg. of lipids and 5 mg. of Z-(14)-heptadecinilbenzoate. This produces a medicine suitable for peroral, parenteral or intranasal use.

The authors have tested the majority of commonly known insect pheromones in the given group (or the synthetic analogues of such pheromones) in order to determine whether they have an antiglucocorticoid effect on the somatic cells of the mammary glands. It transpires that all such pheromones possess the given property to some degree. The choice of pheromone in each particular case is determined by the availability of the pheromones, their capacity for cooperation with the given vehicles, their ability to penetrate biological structures, the safe storage periods of prepared forms of the pheromones, their toxicity, and other factors not of fundamental importance from the point of view of the antihormonal effect which is the subject of the present application. It is obvious that for effective treatment of specific types of illness pheromones may be used in a very large variety of combinations. The choice of combinations of pheromones or their synthetic analogues is determined in accordance with variations in the hydrophobic properties of the components, which factor is critical for their bioaccessibility for various tissues and organs. For example, relatively hydrophilic substances are better at penetrating into the kidneys, whilst relatively hydrophobic substances are more suited to penetrate the liver and brain.

INDUSTRIAL APPLICATION

The enclosed tables 1, 2, 3, and 4 show the results of trials of the proposed medicaments in comparison with analogues and a control group.

Table 1 shows the effectiveness of use of the proposed drug in treatment of various modelled somatic pathologies caused by excessive activity of glucocorticoid hormones.

Table 2 shows the effectiveness of use of the proposed drug in treatment of glucocorticosteroid-induced dermal atrophy (i.e. in suppression of dermal thinning caused by betamazone).

Table 3 shows the antiglucocorticoid (anticatabolic) effectiveness of the proposed drug in treatment of modeled exhausting physical stresses (swimming in a pool).

From Tables 1 and 2 it follows that the proposed drug has, of the drugs tested, the broadest field of effective use in treatment of pathological somatic processes related to the action of glucocorticosteroids and cytotoxic factors; moreover, its effectiveness is considerably higher than that of analogues or preparations in common use.

From Table 3 it follows that the proposed drug is considerably more effective than its analogue in impeding the development of catabolic (glucocorticoid-mediated) changes in the organism during intense physical stress.

TABLE 1

Effectiveness of use of the proposed drug in treatment of various modeled somatic pathologies caused by excessive activity of glucocortoid hormones.

| Model of somatic pathology 1 | Drug used; scheme of administration of drug; dosage 2 | Indices of effect 3 |
|---|---|---|
| Obesity related to excess of glucocorticoids in Zucker-line rats | | Deceleration in weight-gain after 20 days (%) |
| | The proposed drug; given in 10 mg./kg. doses hypodermically once per day | 88% |
| | Mifepriston; given in 10 mg./kg. doses hypodermically once per day (Example 1) | 53% |
| | Control | 0% |
| Stomach ulcer caused by application of 100% acetic acid to the mucous membrane of the stomach, with subsequent daily administration of 2.5 mg.\kg. of hydrocortisone; Wistar rats | | Reversal of delay in healing elicited by chronic administration of hydrocortisone; after 14 days |
| | The proposed drug given intramuscularly in doses of 5 mg.\kg. 3 times per day for 14 days (Example 1) | 87 |
| | Mifepriston; given intramuscularly in 20 mg.\kg. doses 3 times per day for 14 days | 45 |
| | Cimetidine[1]; given intramuscularly in 20 mg.\g. doses 3 times per day for 14 days | 15 |
| | Control | 0 |
| Experimental myocardial infarction; non-pedigree rats | | Reduction in zones of necrosis (%); after: |
| | | 1 day   7 days |
| | Control | 0   0 |
| | The proposed drug; given intramuscularly in a single dose of 10 mg./kg. (Example 3) | 68   89 |
| | Mifepriston (RU486); given intramuscularly in a single dose of 20 mg./kg. | 17   28 |
| | Nitrolgycerine[2]; given intramuscularly in a single injection | 30   55 |
| Involution of the thymus, caused by trauma in non-pedigree rats | | suppression of the involution (% mass) STF[3] |
| | Control (intact rats) | 0   0 |
| | The proposed drug; given intramuscularly in 5 mg./kg. doses 3 | 70   57 |

TABLE 1-continued

Effectiveness of use of the proposed drug in treatment of various modeled somatic pathologies caused by excessive activity of glucocortoid hormones.

| Model of somatic pathology [1] | Drug used; scheme of administration of drug; dosage [2] | Indices of effect [3] |
|---|---|---|
| | times per day for 5 days following traumatization | |
| | Mifepriston; given intramuscularly in 20 mg./kg. doses 3 times per day for 5 days following traumatization | 25  17 |
| | Levamisol[4]; given intramuscularly in 20 mg./kg. doses 3 times per day for 5 days following traumatization | 5  20 |

[1]Cimetidine was used here as an additional comparative preparation; it possesses other (i.e. not related to the antiglucocorticoid effect) mechanisms of action, but is at the present time one of the drugs most widely used for treatment of the given pathology.
[2]Nitroglycerine was used here as an additional preparation for purposes of comparison; it possesses other(i.e. not related to the antiglucocorticoid effect) mechanisms of action, but is at the present time one of the drugs most widely used for treatment of the given pathology.
[3]Concentration of serumal thymic factor.
[4]Levamisol was used here as an additional preparation for purposes of comparison; it possesses other (i.e not related to the antiglucocorticoid effect) mechanisms of action, but is at the present time one of the drugs most widely used for treatment of the given pathology.

TABLE 2

Effectiveness of use of the proposed drug in treatment of glucocorticosteroid-induced dermal atrophy (i.e. in suppression of dermal thinning caused by betamazone).

| Drug used; scheme of administration of drug; dosage[5] | Suppression of dermal thinning (atrophy) caused by betamazone[6] (%) |
|---|---|
| Control | 0 |
| Mifepriston (RU486); 1.5 nanometers/cm² | 7 |
| The proposed drug; 0.5 nanometers/cm² (Example 2) | 87 |
| 1.25-dihydroxyvitamin D3[7]; 1 nanometer/cm² | 65 |

[5]The preparations were administered daily for 10 days, parallel to administration of betamazone. For these trials C3H mice were used (8–10 mice in each group).
[6]Betamazone was administered daily in doses of 2.5 nanometer/cm² for 10 days.
[7]1.25-dihydroxyvitamin D3 was used here as an additional comparative preparation; it possesses other (i.e. not related to the antiglucocorticoid effect) mechanisms of action, but is at the present time one of the drugs most widely used for treatment of the given pathology.

TABLE 3

Antiglucocorticoid (anticatabolic) effectiveness of the proposed drug in treatment of modelled exhausting physical stressed (swimming in a pool).

| Drug used; dosage; scheme of administration[8] | Change in muscular mass (%, after 7 days) | Change in myofibrillar protease[9] (%, after 7 days) | Change in activity of glucocorticoid receptors in leukocytes[10] (%, after 7 days) |
|---|---|---|---|
| Intact animals | 0 | 0 | 0 |
| Control | −10 | +20 | +35 |
| The proposed drug; 10 mg./kg. given perorally 5 minutes after end of strenuous activity | +20 | 0 | 0 |
| Mifepriston (RU486); 20 mg./kg. given perorally 5 minutes after end of strenuous activity | +5 | +7 | +20 |

[8]For these trials use was made of non-pedigree rats (6–8 rats in each group).
[9]This is one of the most important biochemical indices of the catabolic effect of glucocorticoids on myocytes.
[10]This indicates the level of activity of hormone-receptor interaction and the level of influence of the hormone on muscular cells.

In addition to specific results obtained from the experiments conducted above, constant observation was made of side effects and toxic effects such as irritation of the skin and mucous membranes; disbalances of the cardiovascular, digestive and excretory systems; allergic reactions; and so on. The therapeutic index of the proposed drug was 100–300, which is a considerably broader range than the therapeutic index of mifepriston (RU486). Monitoring of the level of sexual steroids and mineralocorticoids in the blood of animals used in the trials did not reveal any changes during use of the proposed drug.

In our opinion the proposed drug meets all the criteria for worthiness of a patent. It is: a) new (from the sources of information available to us, we are not aware of other instances of use of insect pheromones as antihormonal medicaments); b) is suitable for industrial production (as is convincingly demonstrated by the results adduced in the examples and tables); and c) evinces a degree of inventiveness (i.e. is not obvious to a specialist).

The latter statement can be substantiated with the following arguments:

1) As far as the authors are aware, none of the commonly known non-steroid glucocorticoid preparations suppresses bacteria and viruses or induces lysis of erythrocytes as a result of its antiglucocorticoid effect, i.e. until the present time the link between the above-named biological properties of pheromones (i.e. properties named in the section called 'technology') and the anticorticoid effect has not been observed.

2) The biological properties of the given group of pheromones (properties indicated in the section called 'technology', namely: suppression of bacteria and viruses, induction of lysis of erythrocytes) are displayed only in concentrations several tens of times higher than those at which the glucocorticoid effect of the pheromones is observed (as follows from the results of the tests given in the tables). From the point of view of classical endocrinology, the latter fact is an indicator of the non-specificity of the given properties (i.e. suppression, induction). This is additional proof of the fact that the earlier known properties of pheromones have no relation to the antiglucocorticoid effect of pheromones.

3) It is commonly known that neither viruses nor bacteria either possess receptors sensitive to glucocorticoids or synthesize glucocorticoids; it follows that viruses and bacteria have no points of leverage either on glucocorticoid hormones or, accordingly, on antiglucocorticoids.

4) It is commonly known that erythrocytes have no nucleus; thus they have no point of leverage on glucocorticoids and do not synthesize receptors sensitive to glucocorticoids. Thus an effect of this powerful nature (i.e. lysis of the membrane) cannot be caused by the action of anticorticoids.

It would be possible to adduce other strong arguments for the unexpected and non-obvious nature (i.e. not obvious to the specialist) of the use of pheromones as antiglucocorticoid medicaments, i.e. arguments showing that the proposed drug meets the required level of inventiveness.

Reference literature.

1) "Modifiers of steroid-hormone metabolism: a review of their chemistry, biochemistry and clinical operations". J. Steroid Biochem, vol. 5, p. 501, 1974.
2) W. L. Duax, J. F. Griffin, C. M. Weeks, Wawrzak. "The mechanism of action of steroid antagonist: insights from crystallographic studies". J. Steroid Biochem, vol. 31, pp. 481–492, 1988.
3) C. M. Bamberger and G. P. Chrousos. "Glucocorticoid receptor and RU4 man". In: Steroid receptor and antihormones. Annals of New York Academy of Science, vol. 761, pp. 296–310, 1995.
4) G. O. Potts, J. E. Creange, H. R. Hording, H. P. Shahe. "Trilostane, an orally active inhibitor of steroid biosynthesis". Steroids, vol. 32, p.257.
5) V. P. Golikov. "Receptor mechanisms of the glucocorticoid effect". Moskovskaya Meditsina, 1990.
6) H. J. Klosterterboer, G. H. Deckers, M. E. de Gooer, R, Dijkema, E. O. M. Orlemans, W. G. E. J. Schoonen. "Pharmacological properties of a new selective antiprogesten: Org 33628". In: Steroid receptor and antihormones. Annals of New York Academy of Science, vol. 761, pp. 192–201, 1995.
7) V. N. Burov, A. P. Sazon. Biologically active substances in the protection of plants. Moscow, 1987, pp. 96–116.
8) Ibid, p. 79.
9) Insect Pheromone Technology: chemistry and application. Washington, ??.
10) R. O. Potts, M. L. Francoer. Topical pharmacuetical containing penetration-enhancers. Eur. Pat. Appl. EP 331382(C1. A61 K47/00/06 September 1989, U.S. Pat. No. 161,926, Feb. 29, 1988.
11) M. J. Pringle, K. B. Brown, K. Miller. "Can the lipid theories of anesthesia account for the cut off in anesthetic potency in homologous series of alcohols?". Mol. Pharmacol, 1981, vol. 19, No. 1, pp. 49–55.
12) T. Nanba, Y. Hattori, Y. Tsuda, H. Miyaji. "Dentifrices containing fatty acids and unsaturated alcohols for dental caries control". Jpn Kokai Tokio Koho JP 63 88123 [88 88123] (CIA 61K31/20) Apr. 19, 1988.
13) J. Sands, D. Auperin, W. Snipes. "Extreme sensitivity of enveloped viruses, including herpes simplex, to long-chain unsaturated monoglycerides and alcohols". Antimicrob. Agent Chemother, vol. 15, No. 1, pp. 67–73.
14) J. Sands, P. Landin, D. Auperin, A. Rheinhardt. "Enveloped virus inactivation by fatty acid derivatives". Antimicrob. Agent Chemother, vol. 15, No. 1, pp. 134–136.
15) Osirio e Castro et al. "Hemolysis of erythrocytes and fluorescence polarization changes elicited by peptide toxins, aliphatic alcohols related glycols and benzylidene derivatives". Biochem. Biophys, Acta, 1990, vol. 1029, No. 2, pp. 252–258.

We claim:

1. A method for treating obesity collateral to elevated glucocorticoid levels comprising administering to a patient in need of such treatment a therapeutic amount of an anti-glucocorticoid, non-steroidal insect sex pheromone selected from $C_{10}$–$C_{21}$ linear hydrocarbon chain unsaturated aliphatic alcohols, aldehydes and ethers.

2. A method for treating stomach ulcer collateral to elevated glucocorticoid levels comprising administering to a patient in need of such treatment a therapeutic amount of an anti-glucocorticoid, non-steroidal insect sex pheromone selected from $C_{10}$–$C_{21}$ linear hydrocarbon chain unsaturated aliphatic alcohols, aldehydes and ethers.

3. A method for treating myocardial infarction collateral to elevated glucocorticoid levels comprising administering to a patient in need of such treatment a therapeutic amount of an anti-glucocorticoid, non-steroidal insect sex pheromone selected from $C_{10}$–$C_{21}$ linear hydrocarbon chain unsaturated aliphatic alcohols, aldehydes and ethers.

4. A method for treating dermal thinning collateral to elevated glucocorticoid levels comprising administering to a patient in need of such treatment a therapeutic amount of an anti-glucocorticoid, non-steroidal insect sex pheromone selected from $C_{10}$–$C_{21}$ linear hydrocarbon chain unsaturated aliphatic alcohols, aldehydes and ethers.

5. A method for increasing skeletal muscle mass comprising administering to a patient in need of such treatment a therapeutic amount of a non-steroidal insect sex pheromone selected from $C_{10}$–$C_{21}$ linear hydrocarbon chain unsaturated aliphatic alcohols, aldehydes and ethers.

* * * * *